United States Patent
D'Auria et al.

(10) Patent No.: US 7,964,386 B2
(45) Date of Patent: Jun. 21, 2011

(54) PROCESS OF IMMOBILIZING BIOMOLECULES IN POROUS SUPPORTS BY USING AN ELECTRONIC BEAM

(75) Inventors: Sabato D'Auria, Olevano Sul Tusciano (IT); Stefano Marco Borini, Turin (IT); Andrea Mario Rossi, Turin (IT); Mosè Rossi, Arco Felice Pozzuoli (IT)

(73) Assignee: Consiglio Nazionale delle Ricerche, Rome (IT)

( * ) Notice: Subject to any disclaimer, the term of this patent is extended or adjusted under 35 U.S.C. 154(b) by 946 days.

(21) Appl. No.: 11/791,952

(22) PCT Filed: Nov. 29, 2005

(86) PCT No.: PCT/IT2005/000702
§ 371 (c)(1),
(2), (4) Date: Aug. 24, 2007

(87) PCT Pub. No.: WO2006/059356
PCT Pub. Date: Jun. 8, 2006

(65) Prior Publication Data
US 2009/0036326 A1 Feb. 5, 2009

(30) Foreign Application Priority Data
Dec. 3, 2004 (IT) .............................. NA2004A0067

(51) Int. Cl.
*C12M 1/00* (2006.01)

(52) U.S. Cl. .................................................. 435/283.1
(58) Field of Classification Search .................. None
See application file for complete search history.

(56) References Cited

U.S. PATENT DOCUMENTS

| 6,248,539 B1 * | 6/2001 | Ghadiri et al. ................. 435/7.1 |
| 2003/0068446 A1 | 4/2003 | Mirkin et al. |
| 2004/0091421 A1 * | 5/2004 | Aston et al. .................. 424/1.11 |
| 2004/0242023 A1 * | 12/2004 | Yan et al. ...................... 438/780 |
| 2009/0041908 A1 * | 2/2009 | Canham ....................... 426/107 |

FOREIGN PATENT DOCUMENTS

| EP | 1186888 | 3/2002 |
| WO | 03/087291 | 10/2003 |

OTHER PUBLICATIONS

"Chemical and Biological Applications of Porous Silicon Technology," Stewart et al., Advanced Materials, vol. 12, No. 12, Jun. 16, 2000, pp. 859-869, XP000959546.

"Porosity and Pore Size Distributions of Porous Silicon Layers," Herino et al., Journal of The Electrochemical Society, vol. 134, No. 8A, Aug. 1, 1987, pp. 1994-2000, XP002013260.

* cited by examiner

*Primary Examiner* — Ann Y Lam
(74) *Attorney, Agent, or Firm* — Young & Thompson

(57) ABSTRACT

A process of immobilizing biomolecules on a support of porous silicon locally activated by using an electronic beam, activated supports of porous silicon produced in this way, and their use for sensorics applications in biological, medical fields.

2 Claims, 3 Drawing Sheets

PROCESS OF IMMOBILIZING BIOMOLECULES IN POROUS SUPPORTS BY USING AN ELECTRONIC BEAM

The present invention relates to nanoelectronics and biosensorics and particularly a process of immobilizing biomolecules on a support of porous silicon locally activated by an electronic beam. The present invention further provides activated supports of porous silicon produced by the process mentioned above as well as their use for manufacturing optical, electronic devices for sensorics in the biological, medical field, and nanobioelectronic devices as well.

The immobilization of biomolecules to solid supports and the capability of locating such biomolecules in specific predetermined areas are essential in nanoelectronics and biosensorics. Only a few methods able to locate and immobilize biomolecules with a sub-micrometric resolution are known; such methods are mainly based on the use of pens for Atomic Force Microscopy (AFM) as in case of Dip Pen Nanolithography (DPN), local anode oxidation, or nanografting. Further methods recently proposed utilizes non-standard-equipments such as "nanopipets", however, these approaches often require a chemical modification of the supporting surface, thus increasing cost and time. Therefore, there is a particular need for the setup of new methods that makes the activation of solid supports with biomolecules easier and more specific, and at the same time allows activated supports that can be used in nanoelectronics and biosensorics to be provided.

In the light of the state of art the inventors of the present invention have devised a new process of immobilizing biomolecules to activated supports of porous silicon able to overcome the problems mentioned above.

Therefore, an object of the present invention is a process that allows biomolecules to be immobilized to a support of porous silicon in defined areas with a sub-micrometric three-dimensional resolution by an electronic beam produced by a standard Scanning Electronic Microscope (SEM).

In particular, biomolecules in contact with the silicon support are immobilized specifically to the irradiated areas which are determined on a sub-micrometric basis by utilizing the high resolution of the electronic beam. The depth of the irradiated areas is also controlled, thus providing biomolecular structures immobilized in three dimension. The following radiation to areas which are near or not on the same silicon support allows different biomolecules to be immobilized, thus creating a so-called "lab-on-chip".

Thus, the process which is object of the present invention allows the wide inside surface of porous silicon to be utilized for providing high immobilized biomolecule concentrations and/or three-dimensional patterns also of different biomolecules with a precise location.

Therefore, a further object of the present invention is an activated support of porous silicon including at least one biomolecule selected from the group comprising peptides, enzymes, antibodies, DNA, RNA, PNA, peptameres, etc. as well as their use to provide biosensors on porous silicon or bioelectronic devices (such as single-protein transistors) on porous silicon.

Further features of the present invention will be more readily apparent from the following detailed description as well as the examples and the accompanying drawings in which.

Figure 1A:
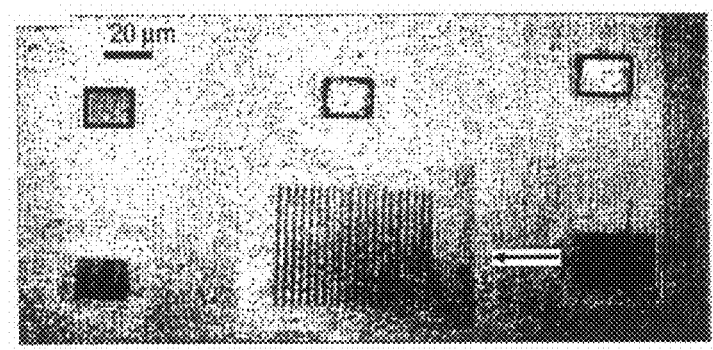
FIG. 1A is an image provided by the optical microscope and showing a protein pattern crated on the supporting surface of porous silicon by an electronic beam under several conditions and after exposure to a solution of glutamine-binding protein for an incubation time of 1 hour at 37° C. The arrow indicates the enlargement of a single pattern.

As known, porous silicon obtained by anodization of silicon doped in hydrofluoric acid is a very interesting support to make bio-devices owing to its characterizing proved biocompatibility and the wide inside surface (of the order of 200 m$^2$/cm$^3$).

A chip of porous silicon is able to bind biomolecules by a hydrophobic bond all over its surface or in its interior, while a chip activated by light binds biomolecules covalently on the surface.

The inventors of the present invention have shown surprisingly that there is a highly preferential interaction between biomolecules and areas of porous silicon irradiated by an electronic beam (EBAPS). Biomolecules binds specifically to EBAPS and are able to enter the porous material. The size of EBAPS areas is determined directly by the interaction of the electronic beam with porous silicon. Therefore, upon moving the electronic beam on the support it is possible to define the patterns to which biomolecules will bind, and upon adjusting the power of the electronic beam it is possible to change the depth of penetration of electrons and then to control the third dimension of the biomolecule EBAPS patterns.

Once one biomolecule is bound to a determined area of the support it is possible to bind one more biomolecule by the same way to another area which is far or near the first area so that it is possible to form a series of spots with different properties and uses, in other words a "lab-on-chip".

A suitable selection of process parameters (such as power and dose during the radiation by electronic beam, and incubation time) allows the density of biomolecules bound to porous silicon to be adjusted under control.

Biomolecules such as peptides, enzymes and even modified antibodies, DNA, RNA, PNA, peptameres, etc. can be bound specifically to porous silicon to provide predetermined patterns with the possibility of producing even more patterns of different biomolecules on the same chip.

Therefore, the chips can be used to produce biosensors on porous silicon or bioelectronic devices (such as single-protein transistors) on porous silicon.

The object of the present invention is a process comprising the following steps:

A) providing a layer of porous silicon by anodization of silicon doped in hydrofluoric acid;
B) drying the sample produced in step A by nitrogen flow;

C) inserting the sample produced in step B into electronic microscope (SEM) and irradiating areas having a minimum size lower than one µm and any spacing by an electronic beam with an electronic surface dose between 1 mC/cm² and 1 C/cm²;

D) extracting the sample produced in step C from SEM and incubating it in biomolecule solution at a concentration between 0.01 mg/ml and 100 mg/ml for an incubation time between 1 second and 2 hours at a temperature between 10° C. and 40° C.;

E) rinsing repeatedly the sample produced in step D by deionised water and next drying by nitrogen flow.

The chips of porous silicon produced as above include a pattern of at least one biomolecule selected from the group consisting of peptides, enzymes, antibodies, DNA, RNA, PNA, peptameres.

The present invention further relates to the use of chips of porous silicon produced as above to provide biosensors on porous silicon and/or bioelectronic devices and/or single-protein transistors on porous silicon.

In a preferred embodiment the layer of porous silicon is produced in step A by electrochemical etching of boron-doped monocrystalline silicon sample with a resistivity of 0.008-0.012 ohm cm by using a solution of HF[50%]:EtOH (1:1 by volume) and current density of 400 mA/cm². The sample, after anodization, is dried by a nitrogen flow in step B. In step C the sample is inserted into the electronic microscope (SEM) and the movement of the incident electronic beam to the sample is controlled so as to irradiate rectangles 500 nm wide, 30 micrometers long, with spacing of 1 micrometer, beam current of 3.5 nA, acceleration voltage of 15 kV, and surface electronic dose of 140 mC/cm².

In step D the sample extracted from SEM is incubated in a solution including glutamine-binding protein and/or glucose-binding protein marked by rhodamine for one hour at 37° C. In step E the sample is rinsed carefully several times in deionised water and dried by a nitrogen flow.

EXAMPLE 1

Immobilization of Proteins Along Sub-micrometric Lines on Porous Silicon

A porous silicon layer was produced by electrochemical etching of boron-doped monocrystalline silicon sample with a resistivity of 0.008-0.012 ohm cm by using a solution of HF[50%]:EtOH (1:1 by volume) and current density of 400 mA/cm². After anodization the sample was dried by a nitrogen flow and inserted into the electronic microscope (SEM). The movement of the electronic beam incident onto the sample could be controlled by nanolithography system NPGS (NanoPattern Generator System, by J C Nabity) so that rectangles 500 nm wide, 30 cm long, with a spacing of 1 micrometer can be irradiated. A square areas with a side of 30 micrometers was further irradiated. The current of the beam was 3.5 nA, the acceleration voltage was 15 kV, and the electronic surface dose was 140 mC/cm².

The sample was then extracted from SEM and brought immediately into contact with a solution of glutamine-binding protein marked by rhodamine. After an incubation time of one hour at 37° C. the sample was rinsed carefully several times in deionised water and dried by a nitrogen flow.

As shown in FIG. 1A, the examination by optical microscope revealed that the irradiated areas were easily visible, and the use of an objective 100× allowed sub-micrometric lines to be distinguished.

Figure 1B:
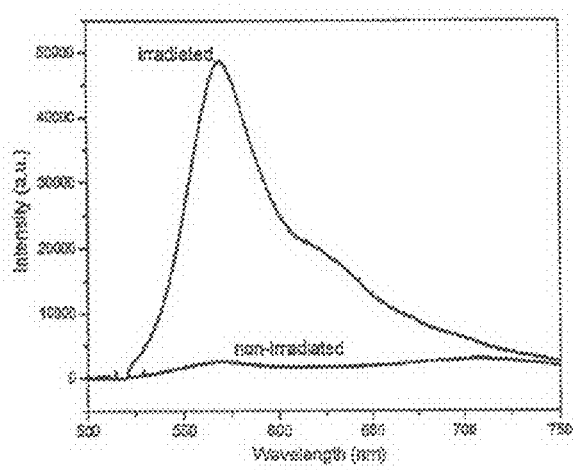
FIG. 1B shows the fluorescence spectrum provided by two areas of the same sample of porous silicon, one area being irradiated by an electronic beam with energy of 15 keV and a dose of 140 mC/cm$^2$ after exposure to a solution of glutamine-binding protein marked by rhodamine for 1 hour at 37° C.

The fluorescence analysis on EPABS containing the immobilized protein by using a micro-photoluminescence apparatus shown in FIG. 1B revealed the fluorophor signals from the irradiated areas. The comparison between the intensity of the fluorescence signal from the irradiated area along sub-micrometric lines and the intensity of the signal from the total irradiated area gave as result that the proteins were bound specifically to EBAPS areas following the sub-micrometric definition during the radiation.

EXAMPLE 2

Figure 2:
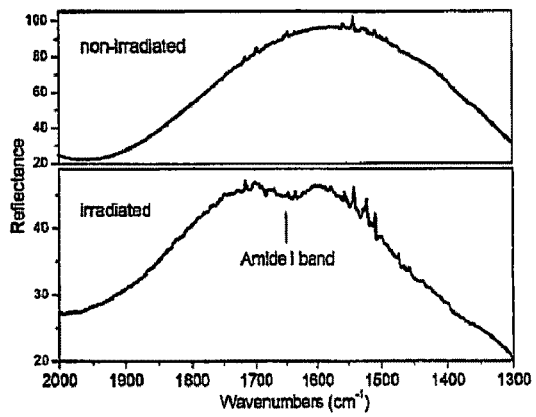
FIG. 2 shows FTIR-spectrum (Fourier Transform Infra-Red) provided by two areas of the sample of porous silicon, one area irradiated by an electronic beam with energy of 15 keV and a dose of 140 mC/cm$^2$ after exposure to a solution of glutamine-binding protein marked by rhodamine for 1 hour at 37° C.

Immobilization of Proteins on the Inside Surface of Porous Silicon at Different Depths A layer of porous silicon with a thickness of about 5 micrometers was produced by using the method described in Example 1. The sample was then inserted into SEM and two square areas with a side of 20 micrometers were irradiated under the same conditions as Example 1 but by two different acceleration voltages: 5 kV and 15 kV. The sample was then extracted from SEM and brought into contact with a solution of glucose-binding protein marked with fluorescin for an incubation time of one hour at room temperature. The microfluorescence examination as shown in FIG. 2 indicates that the intensity of the signal is greater in the case of an area irradiated by 15 kV.

Figure 3A:
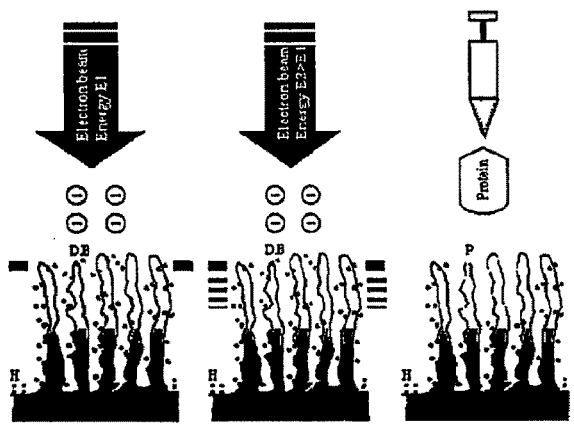
FIG. 3A shows a diagram of the process of activating the layer of porous silicon and the next bond with biomolecules.
Figure 3B:
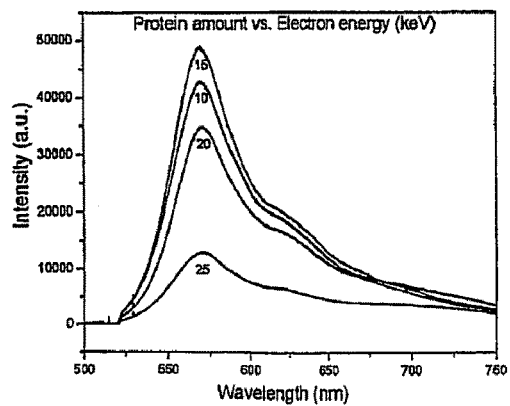
FIG. 3B shows the fluorescence spectrum provided by different areas of the same sample of porous silicon after irradiation with an electronic dose of 140 mC/cm$^2$ and exposure to a solution of glutamine-binding protein marked by rhodamine for 1 hour at 37° C.

FIG. 3 shows the results of a similar work on another sample of porous silicon irradiated in three areas with three different acceleration voltages (10 kV, 15 kV, 20 kV) and brought into contact with a solution of glutamine-binding protein marked with rhodamine. In this case, the fluorescence signal increases as the voltage rises from 10 kV to 15 kV and decreases as the voltage rises from 15 kV to 20 kV.

As the acceleration voltage determines the depth of penetration of the electrons into the substrate, these results indicate that the proteins bind themselves to the inside surface of the porous silicon following the path of the electrons during the irradiation. Over a determined voltage (for example 20 kV) electrons move very swift and their interaction with the porous material decreases. Accordingly, the surface activated by the electronic beam decreases, thus causing the binding proteins to be reduced.

The suitable variation of the acceleration voltage can then control the depth of the protein patterns.

EXAMPLE 3

Immobilization of Different Proteins on the Inside Surface of Porous Silicon at Different Depths The two proteins described in Example 2 were immobilized on the same chip after several irradiations so that a chip for the simultaneous detecting of the presence of glucose and glutamine is produced.

EXAMPLE 4

Control of the Density of the Proteins Bound to Porous Silicon

Figure 4:
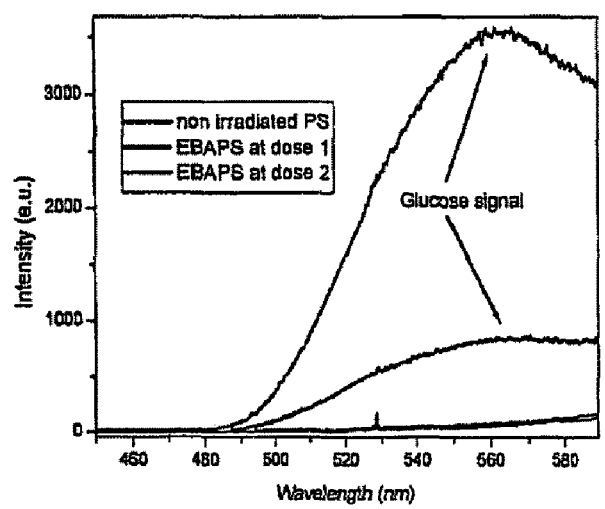
FIG. 4 shows the fluorescence spectrum provided by different areas of the same sample of porous silicon activated by different electronic doses (D1=70 mC/cm$^2$, D2=140 mC/cm$^2$) and made functional by glucose-binding proteins.

A sample of porous silicon produced under the same conditions as mentioned in Example 1 was irradiated at two areas by using two different electronic doses: 70 mC/cm² and 140 mC/cm². The acceleration voltage and the beam current were fixed at 20 kV and 3.5 nA, respectively. The sample was brought into contact with the solution of glutamine-binding protein marked with rhodamine for one hour. The microfluorescence examination showed that the intensity of the signal increases remarkably as the dose increases (FIG. 4).

In another experiment the fluorescence signals from samples of porous silicon irradiated under the same conditions but exposed to the protein solution during different incubation times were compared. The microfluorescence examination showed that the intensity of the signal increases as the incubation time increases.

Therefore, the suitable variation of electron dose and incubation time can cause the density of the proteins bound to EBAPS to change under control.

BIBLIOGRAPHY

K.-B. Lee, S.-J. Park, C. A. Mirkin, J. C. Smith, M. Mrksich, *Science* 295, 1702 (2002).
T. Yoshinobu, J. Suzuki, H. Kurooka, W. C. Moon, H. Iwasaki, *Electrochim. Acta* 48 3131 (2003).
K. Wadu-Mesthrige, N. A. Amro, J. C. Garno, S. Xu, G.-Y. Liu, *Biophys. J.* 80, 1891 (2001).
H. Taha, R. S. Marks, L. A. Gheber, I. Rousso, J. Newman, C. Sukenik, A. Lewis, *Appl. Phys. Lett.* 83, 1041 (2003).
L. T. Canham, *Adv. Mater.* 7, 1033 (1995).
L. T. Canham, in *Properties of Porous Silicon*, L. Canham, Ed. (Short Run Press, London, 1997), vol. 18, pp. 371-376; V. S.-Y. Lin, K. Motesharei, K. S. Dancil, M. J. Sailor, M. R. Ghadiri, *Science* 278, 840 (1997); M. P. Stewart, J. M. Buriak, *Adv. Mater.* 12, 859 (2000); S. E. Létant, B. R. Hart, A. W. Van Buuren, L. J. Terminello, *Nat. Mater.* 2, 391 (2003).
R. Hérino, G. Bomchil, K. Barla, C. Bertrand, J. L. Ginoux, *J. Electrochem. Soc.* 134, 1994 (1987).

The invention claimed is:

1. A process of immobilizing biomolecules on porous silicon supports comprising:
   A) providing a porous silicon layer on a support by anodization of silicon doped in hydrofluoric acid;
   B) drying the silicon layer support produced in step A by nitrogen flow;
   C) inserting the silicon layer support produced in step B into a scanning electron microscope (SEM) and irradiating areas of the silicon layer having a minimum size lower than one μm and any spacing by an electronic beam with an electronic surface dose between 1 mC/cm$^2$ and 1 C/cm$^2$;
   D) extracting the silicon layer support produced in step C from the SEM and incubating the silicon layer support in a biomolecule solution having a concentration between 0.01 mg/ml and 100 mg/ml for an incubation time between 1 second and 2 hours at a temperature between 10° C. and 40° C.;
   E) rinsing repeatedly the silicon layer support produced in step D by deionised water and drying by nitrogen flow.

2. The process according to claim 1, wherein
   the layer of porous silicon is produced in step A by electrochemical etching of boron-doped monocrystalline silicon sample with a resistivity of 0.008-0.012 Ohm cm by using a solution of HF[50%]:EtOH (1:1 by volume) and current density of 400 mA/cm$^2$,
   the silicon layer support, after anodization, being dried by a nitrogen flow in step B,
   the silicon layer support being inserted into the scanning electron microscope (SEM) in step C and the movement of the incident electronic beam to the sample being controlled so as to irradiate rectangles 500 nm wide, 30 micrometers long, with spacing of 1 micrometer, beam current of 3.5 nA, acceleration voltage of 15 kV, and surface electronic dose of 140 mC/cm$^2$,
   the silicon layer support extracted from the SEM in step D being incubated in a solution including glutamine-binding protein and/or glucose-binding protein marked by rhodamine for one hour at 37° C., and
   the silicon layer support being rinsed carefully several times in deionised water and dried by a nitrogen flow in step E.

* * * * *